(12) United States Patent
Scott et al.

(10) Patent No.: US 10,543,215 B2
(45) Date of Patent: Jan. 28, 2020

(54) COMBINATION THERAPY OF CARDIAC MYOSIN ACTIVATOR AND SINUS NODE IF CURRENT INHIBITOR

(71) Applicant: AMGEN INC., Thousand Oaks, CA (US)

(72) Inventors: Robert Andrew Donald Scott, Thousand Oaks, CA (US); Scott Wasserman, Newbury Park, CA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

(21) Appl. No.: 15/578,305

(22) PCT Filed: Jun. 24, 2016

(86) PCT No.: PCT/US2016/039198
§ 371 (c)(1),
(2) Date: Nov. 30, 2017

(87) PCT Pub. No.: WO2016/210240
PCT Pub. Date: Dec. 29, 2016

(65) Prior Publication Data
US 2018/0140611 A1    May 24, 2018

Related U.S. Application Data

(60) Provisional application No. 62/185,306, filed on Jun. 26, 2015.

(51) Int. Cl.
| | | |
|---|---|---|
| *A61K 31/55* | (2006.01) | |
| *A61K 31/496* | (2006.01) | |
| *A61K 45/06* | (2006.01) | |
| *A61P 9/04* | (2006.01) | |
| *A61K 9/20* | (2006.01) | |

(52) U.S. Cl.
CPC .......... *A61K 31/55* (2013.01); *A61K 9/2013* (2013.01); *A61K 9/2054* (2013.01); *A61K 31/496* (2013.01); *A61K 45/06* (2013.01); *A61P 9/04* (2018.01)

(58) Field of Classification Search
None
See application file for complete search history.

(56) References Cited

U.S. PATENT DOCUMENTS

| | | |
|---|---|---|
| 5,296,482 A | 3/1994 | Peglion et al. |
| 2006/0014761 A1* | 1/2006 | Morgan ............... C07D 211/56 514/256 |

FOREIGN PATENT DOCUMENTS

| | | |
|---|---|---|
| EP | 0534859 A1 | 3/1993 |
| WO | WO-2006/009726 A2 | 1/2006 |
| WO | WO-2014/152236 A1 | 9/2014 |

OTHER PUBLICATIONS

Ferrari et al (Pharmacological Res 53:435-439, 2006) (Year: 2006).*
Derwent Summary (Derwent Accession No. 2008-L15469)—summarizing Gu et al (CN 101095682) (Year: 2008).*
Cleland et al., The effects of the cardiac myosin activator, omecamtiv mecarbil, on cardiac function in systolic heart failure: a double-blind, placebo-controlled, crossover, dose-ranging phase 2 trial, Lancet, 378(9792):676-83 (2011).
International Application No. PCT/US2016/039198, International Search Report and Written Opinion, dated Aug. 26, 2016.
McAlister et al., Meta-analysis: beta-blocker dose, heart rate reduction, and death in patients with heart failure, Ann. Intern. Med., 150(11):784-94 (2009).
Nakou et al., New therapeutic options in heart failure. What's on the horizon? An overview, Int. J. Cardiol., 170(2):95-106 (2013).
Tamargo et al., New investigational drugs for the management of acute heart failure syndromes, Curr. Med. Chem., 17(4):363-90 (2010).
Zugck et al., Ivabradine treatment in a chronic heart failure patient cohort: symptom reduction and improvement in quality of life in clinical practice, Adv. Ther., 31(9):961-74 (2014).

* cited by examiner

*Primary Examiner* — Craig D Ricci
(74) *Attorney, Agent, or Firm* — Marshall, Gerstein & Borun LLP

(57) ABSTRACT

Disclosed herein are combination therapies for the treatment of heart failure using a cardiac myosin activator, such as omecamtiv mecarbil, and a sinus node If current inhibitor, such as ivabradine. Also disclosed herein are compositions comprising a cardiac myosin activator and a sinus node If current inhibitor.

6 Claims, 2 Drawing Sheets

COMBINATION THERAPY OF CARDIAC MYOSIN ACTIVATOR AND SINUS NODE If CURRENT INHIBITOR

Provided is a combination therapy of a cardiac myosin activator and a sinus node If current inhibitor, and pharmaceutical compositions of the same.

BACKGROUND

Heart failure (HF) is a chronic condition marked by impaired cardiac contractility leading to a systemic reduced organ blood perfusion, uncoupling the consumption and delivery of oxygen to the tissues, and eventually death. Hemodynamic and metabolic compensatory mechanisms are effective in a short-term, however may be deleterious in the long run. Pharmacological treatment of HF is based on partially counteracting the compensatory mechanisms, and improving myocardial contractility. In spite of best available pharmacologic therapy for heart failure which includes ACE-I/ARB, beta blocker, and aldosterone antagonists, morbidity and mortality remains high with approximately 30% of patients being hospitalized for heart failure within 3 months and a 50% survival from diagnosis (enter reference and update statistics based on AHA/ACC HF guidelines).

Compensatory elevated resting heart rate is considered a modifiable risk factor for patients with HF. Beta-blockers have been successful in reducing heart rate, among other actions, and improving morbidity and mortality of HF. However, a significant proportion of patients cannot tolerate the negative inotropic or lusitropic effects of beta-blockers and maintain elevated heart rates even under maximally tolerated dose of these agents. Ivabradine is a specific inhibitor of the If current in the sinoatrial node resulting in heart rate reduction that can result in an associated increase in the diastolic phase of the cardiac cycle and coronary artery filling without a change in myocardial contractility or relaxation. The efficacy and safety of ivabradine in reducing morbidity and mortality in HF was proven as an add-on therapy for patients under maximum tolerated background therapy and persistent elevated resting heart rate (above 70-75 bpm). However, symptomatic bradycardia may result from ivabradine use when the heart rate reduction exceeds the ability of compensatory physiologic mechanisms to maintain sufficient blood pressure.

Myocardial contractility is another target for HF therapies. Cardiac myosin activators like omecamtiv mecarbil are a new mechanistic class designed specifically to improve myocardial contractility. The mechanism of action of myosin activators increases the number of active myosin-actin interactions, resulting in an increase in the systolic ejection time, but not in the velocity of contraction, promoting an increase in stroke volume without significant increase in oxygen consumption. The availability of an oral formulation for chronic use, absence of arrhythmogenic effects, and no increase in myocardium oxygen consumption make omecamtiv mecarbil a promising therapeutic option for HF. An increase in systolic ejection time without a concomitant increase in diastolic time could reduce the time available for coronary artery filling.

Thus, HF remains a high unmet need condition which will benefit from development of additional therapeutic options that improve cardiac contractility while preserving coronary artery flow in diastole. Combination use of ivabradine and omecamtiv mecarbil provides an opportunity for the additive benefits of heart rate reduction and improved myocardial contractility in heart failure as derived from the individual therapies respectively. Additionally, there is an opportunity for mutual risk mitigation as symptomatic bradycardia that may result from ivabradine could be offset by improvements in myocardial contractility seen with omecamtiv mecarbil and reduction in diastolic coronary filling that may result from omecamtiv mecarbil could be offset by increased diastolic coronary filling that may result from ivabradine.

SUMMARY

Provided herein are methods of treating a subject suffering from heart failure comprising administering to the subject a cardiac myosin activator and a sinus node If current inhibitor. In various cases, the subject suffers from one or more of congestive heart failure, systolic heart failure, and heart failure with reduced left ventricular ejection fraction. The methods provided herein can result in a decrease in ischemic events, compared to administration of a cardiac myosin activator (e.g., omecamtiv mecarbil) alone. The methods provided herein can result in a decrease in systolic to diastolic ratio, compared to administration of a cardiac myosin activator (e.g., omecamtiv mecarbil) alone. The methods provided herein can result in a decrease in troponin levels, compared to administration of a cardiac myosin activator (e.g., omecamtiv mecarbil) alone. The methods provided herein can result in an increase in cardiac contractility, compared to administration of a cardiac myosin activator (e.g., omecamtiv mecarbil) alone.

In various cases, the cardiac myosin activator is omecamtiv mecarbil, or a pharmaceutically acceptable salt or hydrate thereof. In various cases, the sinus node If current inhibitor is ivabradine, or a pharmaceutically acceptable salt or hydrate thereof. In some cases, omecamtiv mecarbil and ivabradine are administered sequentially (e.g., omecamtiv before ivabradine or omecamtiv after ivabradine). In other cases, omecamtiv mecarbil and ivabradine are administered simultaneously. The omecamtiv mecarbil and ivabradine can be co-formulated.

In the methods provided herein, the omecamtiv mecarbil and ivabradine can be administered orally, intravenously, subcutaneously, intramuscularly, intrathecally, or via inhalational. In various cases, the omecamtiv mecarbil is administered orally. In various cases, the ivabradine is administered orally. In some cases, each of the omecamtiv mecarbil and ivabradine is administered orally.

In the methods disclosed herein, the omecamtiv mecarbil can be administered at a total daily amount of 10 mg to 200 mg.

In the methods disclosed herein, the ivabradine can be administered at a total daily amount of 2.5 mg to 20 mg.

Further provided herein are pharmaceutical compositions comprising a cardiac myosin activator and a sinus node If current inhibitor. In various cases, the composition can be in the form of a tablet.

In various cases, the cardiac myosin activator is omecamtiv mecarbil, or a pharmaceutically acceptable salt or hydrate thereof. In some cases, the omecamtiv mecarbil is present as omecamtiv mecarbil dihydrochloride hydrate.

In various cases, the sinus node If current inhibitor is ivabradine, or a pharmaceutically acceptable salt or hydrate thereof. In some cases, the ivabradine is present as ivabradine hydrochloride.

In various cases, the composition can further comprise a control release agent; a pH modifying agent; a filler; and a lubricant. In some cases, the control release agent comprises methylcellulose, hydroxypropyl methylcellulose, or a combination thereof. In some cases, the control release agent comprises methylcellulose and hydroxypropyl methylcellulose. In various cases, the pH modifying agent comprises fumaric acid, maleic acid, glutamic acid, tartaric acid, or a combination thereof. In some cases, the pH modifying agent comprises fumaric acid. In various cases, the filler comprises microcrystalline cellulose, lactose monohydrate, or a combination thereof. In various cases, the lubricant comprises magnesium stearate.

Further provided herein is omecamtiv mecarbil, or a pharmaceutically acceptable salt or hydrate thereof, for use in combination with ivabradine, or a pharmaceutically acceptable salt or hydrate thereof, for treating heart failure.

Further provided herein is ivabradine, or a pharmaceutically acceptable salt or hydrate thereof, for use in combination with omecamtiv mecarbil, or a pharmaceutically acceptable salt or hydrate thereof, for treating heart failure.

Further provided herein is a combination therapeutic comprising ivabradine, or a pharmaceutically acceptable salt or hydrate thereof, and omecamtiv mecarbil, or a pharmaceutically acceptable salt or hydrate thereof, as separate entities for oral administration. In some cases, the combination therapeutic is for use in treating heart failure.

DETAILED DESCRIPTION

Figure 1:
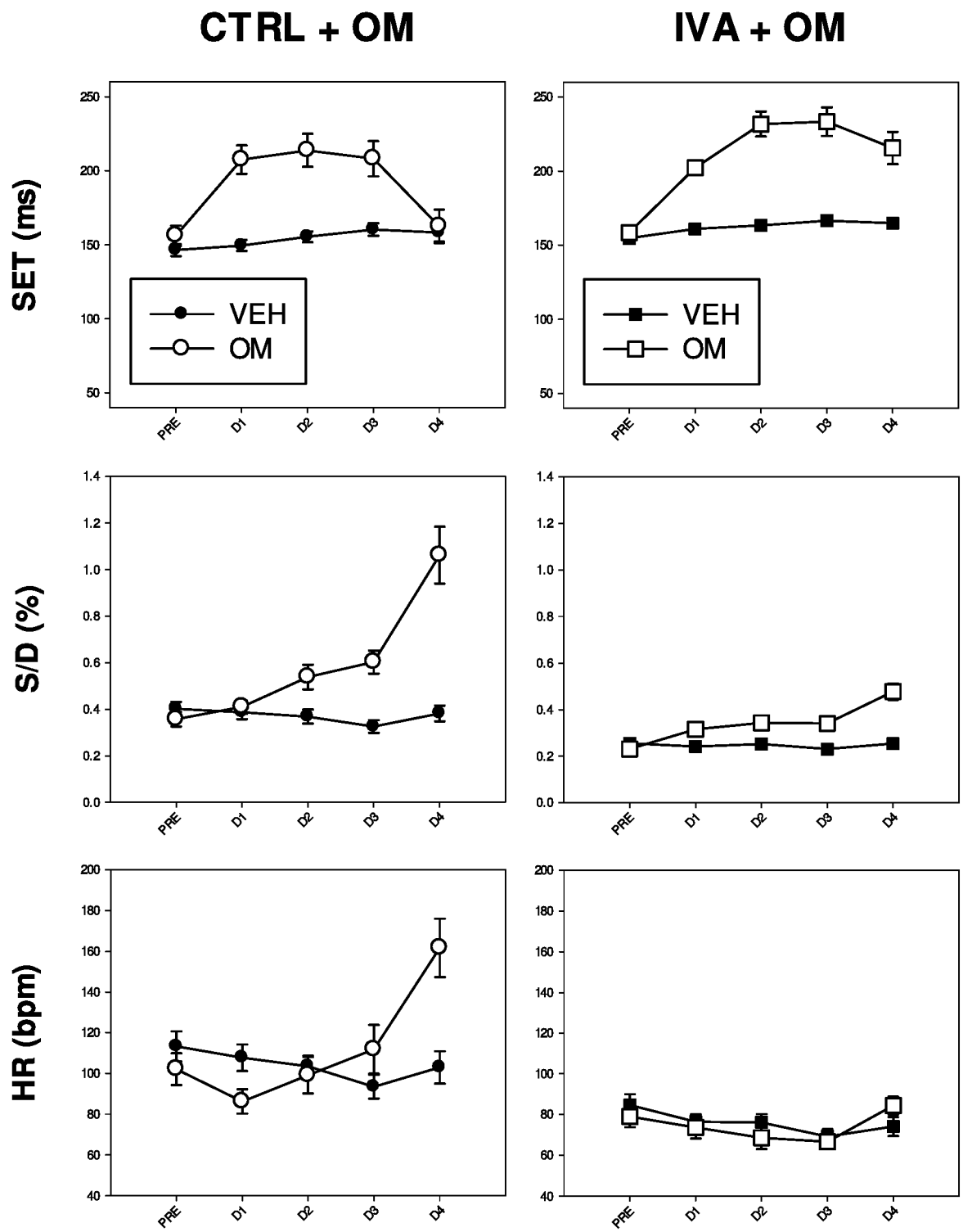
FIG. 1 shows changes in left-ventricular systolic ejection time (SET), mechanical systole-to-diastole ratio (S/D), and heart rate (HR) as measured before and during acute intravenous administration of either vehicle (VEH) or Omecamtiv Mecarbil (OM) in conscious telemetered beagle dogs in the setting of repeated therapy with either Ivabradine (IVA, 5 mg/kg bid PO, for at least 5 days) or placebo (CTRL, sterile water for at least 5 days).
Figure 2:
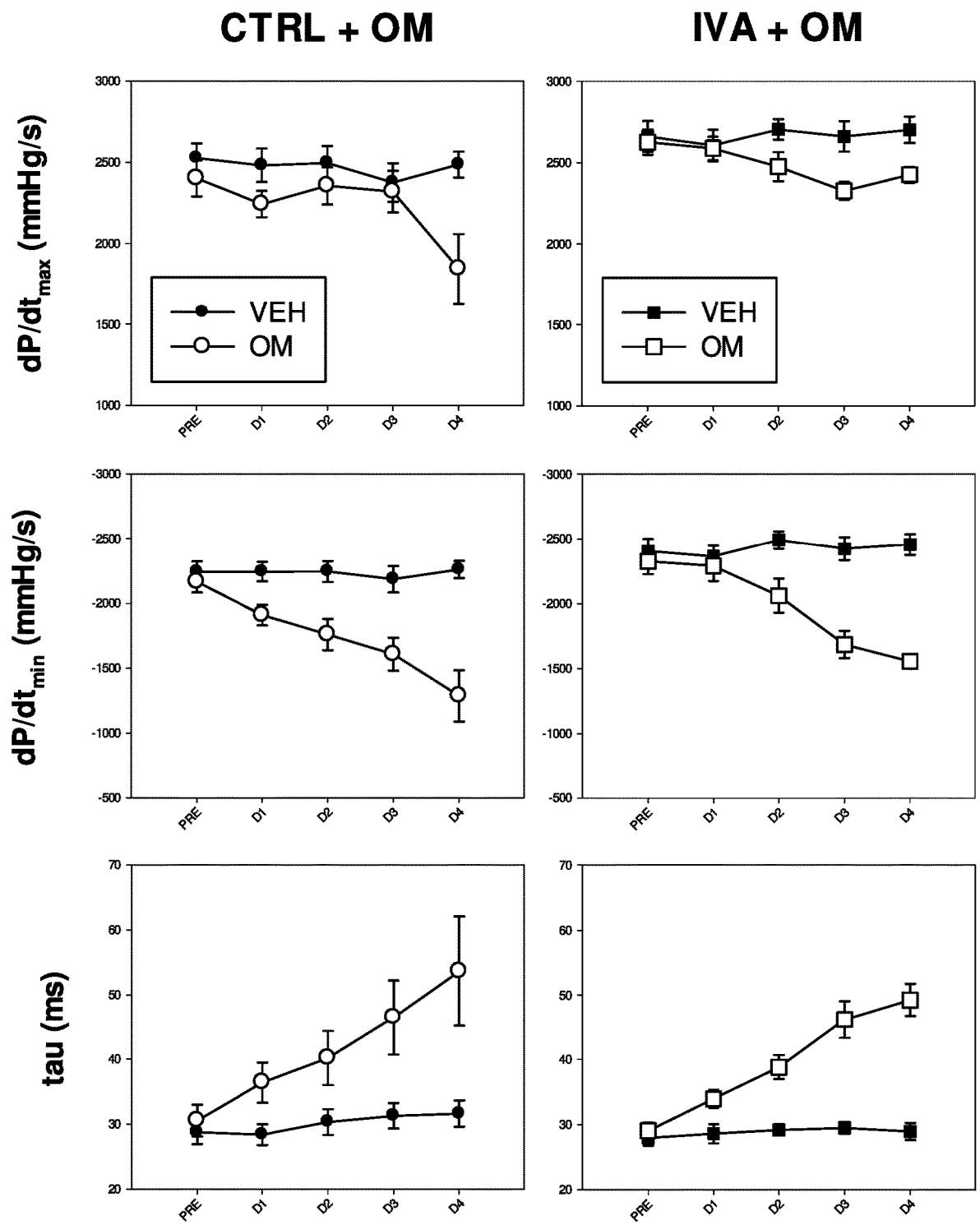
FIG. 2 shows changes in left-ventricular peak rate of pressure change during both systole ($dP/dt_{max}$) and diastole ($dP/dt_{min}$) as well as the time-constant of relaxation (Tau) as measured before and during acute intravenous administration of either vehicle (VEH) or Omecamtiv Mecarbil (OM) in conscious telemetered beagle dogs in the setting of repeated therapy with either Ivabradine (IVA, 5 mg/kg bid PO, for at least 5 days) or placebo (CTRL, sterile water for at least 5 days).

Provided is a combination therapy of a cardiac myosin activator and a sinus node If current inhibitor. In various cases, provided herein is a combination therapy of omecamtiv mecarbil (AMG 423, CK-1827452) or methyl 4-(2-fluoro-3-(3-(6-methylpyridin-3-yl)ureido)benzyl)piperazine-1-carboxylate, having the structure:

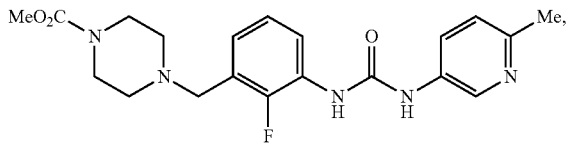 [SMILES: COC(=O)N1CCN(Cc2cccc(NC(=O)Nc3ccc(C)nc3)c2F)CC1]

or a pharmaceutically acceptable salt or hydrate thereof and ivabradine, or 3-{3-[{[(7S)-3,4-dimethoxybicyclo[4.2.0] octa-1,3,5 methyl}(methyl)amino]propyl}-7,8-dimethoxy-1,3,4,5-tetrahydro-2H-3-benzazepin-2-one, having a structure:

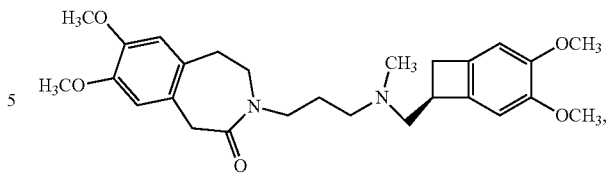

or a pharmaceutically acceptable salt or hydrate thereof. As used throughout, reference to omecamtiv mecarbil herein includes a pharmaceutically acceptable salt or hydrate thereof, unless specifically noted otherwise. Similarly, reference to ivabradine herein includes a pharmaceutically acceptable salt or hydrate thereof, unless specifically noted otherwise.

Omecamtiv mecarbil is a direct activator of cardiac myosin, the motor protein that responsible for cardiac contraction. It is potentially useful as a treatment of heart failure in both intravenous and oral formulations. The preparation and therapeutic use of omecamtiv mecarbil and pharmaceutically acceptable salts thereof have been described in WO 2006/009726.

Ivabradine is a specific inhibitor of the If current in the sinoatrial node resulting in heart rate reduction without impairment of myocardial contractility. The efficacy and safety of ivabradine in reducing morbidity and mortality in HF was proven as an add-on therapy for patients under maximum tolerated background therapy and persistent elevated resting heart rate (above 70-75 bpm).

Sinus node If current inhibitors, more especially ivabradine and its hydrates and salts thereof with a pharmaceutically acceptable acid, more especially its hydrochloride salt, have attractive pharmacological and therapeutic properties which result in heart rate reduction. As lower heart rates have been associated with reductions in heart failure outcomes (Kjekshus J, Gullestad L. *Eur Heart J.* 1999; 1(suppl H):H64-H69; McAlister F A, et al. *Ann Intern Med.* 2009; 150:784-794) these compounds can be useful in heart failure management (reference SHIFT). Additional benefit may also be derived in the treatment of angina pectoris or certain supraventricular rhythm disturbances.

The preparation and therapeutic use of ivabradine and salts thereof with a pharmaceutically acceptable acid, more especially its hydrochloride, have been described in the European patent specification EP 0 534 859.

Described herein is the discovery that a sinus node If current inhibitor, such as ivabradine, is capable of potentiating the effects of a cardiac myosin activator, such as omecamtiv mecarbil. Accordingly, this increased effect is related to a synergy between the active ingredients, i.e. a sinus node If current inhibitor and a cardiac myosin activator.

Heart Failure

Provided herein are methods and compositions for the treatment of heart failure. The contemplated conditions include but are not limited to: acute (or decompensated) congestive heart failure, chronic congestive heart failure, and diseases associated with systolic heart dysfunction.

"Treatment" or "treating" means any treatment of a disease in a patient, including: a) preventing the disease, that is, causing the clinical symptoms of the disease not to develop; b) inhibiting the disease; c) slowing or arresting the development of clinical symptoms; and/or d) relieving the disease, that is, causing the regression of clinical symptoms. Treatment of diseases and disorders herein is intended to also include the prophylactic administration of a pharmaceutical formulation described herein to a subject (i.e., an animal, preferably a mammal, most preferably a human) believed to be in need of preventative treatment, such as, for example, chronic heart failure.

The term "therapeutically effective amount" means an amount effective, when administered to a human or non-human patient, to treat a disease, e.g., a therapeutically effective amount may be an amount sufficient to treat a disease or disorder responsive to myosin activation. The therapeutically effective amount may be ascertained experimentally, for example by assaying blood concentration of the chemical entity, or theoretically, by calculating bioavailability.

The methods and compositions provided herein can result in a reduced incidence of ischemic events, compared to treatment of heart failure by omecamtiv mecarbil alone. In some cases, the methods and compositions provided herein can result in a reduced systolic to diastolic ratio, compared to treatment of heart failure by omecamtiv mecarbil alone. In some cases, the methods and compositions provided herein can result in decreased troponin levels, compared to treatment of heart failure by omecamtiv mecarbil alone.

Pharmaceutical Compositions and Dosing

Provided herein are combination therapies of omecamtiv mecarbil, or a pharmaceutically acceptable salt or hydrate thereof, and ivabradine, or a pharmaceutically acceptable salt or hydrate thereof, for treating heart failure. The two active ingredients can be administered sequentially or in parallel. When in parallel, the actives can be separately administered or co-formulated.

"Pharmaceutically acceptable salts" include, but are not limited to salts with inorganic acids, such as hydrochloride, phosphate, diphosphate, hydrobromate, sulfate, sulfinate, nitrate, and like salts; as well as salts with an organic acid, such as malate, maleate, fumarate, tartrate, succinate, citrate, acetate, lactate, methanesulfonate, p-toluenesulfonate, 2-hydroxyethylsulfonate, benzoate, salicylate, stearate, and alkanoate such as acetate, $HOOC-(CH_2)_n-COOH$ where n is 0-4, and like salts. Similarly, pharmaceutically acceptable cations include, but are not limited to sodium, potassium, calcium, aluminum, lithium, and ammonium. Those skilled in the art will recognize various synthetic methodologies that may be used to prepare non-toxic pharmaceutically acceptable salts.

The dosage of the active (or actives) can be varied according to the nature and severity of the disorder, the administration route and also the age and weight of the patient. In the compositions provided herein, the dose ranges from 10 mg to 200 mg for the cardiac myosin activator (e.g., based upon the weight of the free base activator), such as omecamtiv mecarbil or a pharmaceutically acceptable salt or hydrate thereof, such as omecamtiv mecarbil dihydrochloride hydrate, and from 2.5 to 30 mg of sinus node If current inhibitor (e.g., based upon the weight of the free base inhibitor), such as ivabradine or a pharmaceutically acceptable salt or hydrate thereof, per 24 hours in one or more administrations. In some cases, the sinus node If current inhibitor is ivabradine or a pharmaceutically acceptable salt or hydrate thereof and the ivabradine or a pharmaceutically acceptable salt or hydrate thereof administration dose is from 2.5 to 20 mg or 5 mg to 15 mg, or 10 mg to 15 mg total daily dose (e.g., based upon the weight of the free base ivabradine), once or twice per day. In various cases, the cardiac myosin activator is omecamtiv mecarbil or a pharmaceutically acceptable salt or hydrate thereof, and the daily administration dose is 12.5 mg to 150 mg, 12.5 mg to 100 mg, 12.5 mg to 75 mg, 25 mg to 75 mg, 12.5 mg to 50 mg, or 25 mg to 50 mg (e.g., based upon the weight of the free base omecamtiv mecarbil), once or twice per day.

In some cases, the formulation is a tablet formulation capable of controlled release of the omecamtiv mecarbil or a pharmaceutically acceptable salt or hydrate thereof, optionally further comprising ivabradine or a pharmaceutically acceptable salt or hydrate thereof. The pharmaceutical formulations described herein are capable of releasing omecamtiv mecarbil evenly at a pace controlled by the diffusion of omecamtiv mecarbil through a gel layer formed by the hydration of the control release agents in the tablets. In some embodiments, in conjunction with other above or below embodiments, the present modified release matrix tablets demonstrate a minimal pH-dependent release in-vitro. In some embodiments, in conjunction with other above or below embodiments, complete release of omecamtiv mecarbil is achieved in both pH 2 and 6.8 dissolution medium within 24 hours, which can result in less inter- and intra-subject variability and food effect. It is found that the present modified release matrix tablet dosage form is superior to the former immediate release dosage form in minimizing the plasma peak-trough ratio. As a result, the present modified release matrix tablets reduce plasma concentration fluctuation, leading to reduced side effects, and improved safety and efficacy. It is also expected that the present modified release matrix tablets will improve patient compliance by reducing the dosing frequency. Additionally, the present modified release matrix tablets are physicochemically stable—resulting in no physical attribute, assay, impurity, or dissolution profile changes after storage at 40° C./75% RH for 6 months. Tablet formulations for controlled release of omecamtiv mecarbil are described in WO 14/152236.

In some embodiments, in conjunction with other above or below embodiments, the exposure of omecamtiv mecarbil from two to twelve hours after dosing in humans is between 50 and 800 ng/ml.

In some embodiments, in conjunction with other above or below embodiments, the exposure of omecamtiv mecarbil from two to twelve hours after dosing in humans remains between 100 and 800 ng/ml.

In some embodiments, in conjunction with other above or below embodiments, the omecamtiv mecarbil is released in the following intervals: ≤30% dose dissolved at 1 hour; 30-75% dose dissolved at 3 hours; and ≥80% dose dissolved at 12 hours.

In some embodiments, in conjunction with other above or below embodiments, the omecamtiv mecarbil is released in the following intervals: ≤30% dose dissolved at 2 hours; 30-75% dose dissolved at 6 hours; and ≥80% dose dissolved at 16 hours.

Provided is a pharmaceutical formulation comprising: omecamtiv mecarbil, or a pharmaceutically acceptable salt or hydrate thereof; ivabradine, or a pharmaceutically acceptable salt or hydrate thereof; a control release agent; a pH modifying agent; a filler; and a lubricant.

Control release agent: As used herein, the term "control release agents" refer to agents that facilitate the release of the active ingredient from the present composition in a controlled fashion. In some embodiments, in conjunction with other above or below embodiments, the control release agents form a gel upon hydration. Control release agents include pulluan, dextrin, sodium and calcium acid, polyacrylic acid, polymethacrylic acid, polymethylvinylether co-maleic anhydride, polyvinylpyrrolidone, polyethylene oxide, polyethylene glycol, hydroxypropylcellulose, hydroxypropylmethylcellulose, hydroxyethylcellulose, hydroxymethyl methacrylate, sodium carboxymethylcellulose, calcium carboxymethylcellulose, methylcellulose, maltodextrin, xanthan gum, tragacanth gum, agar, gellan gum, kayara gum, alginic acids, pectins, pre-gelatinized starch, polyvinyl alcohol, carboxymethylethylcellulose, cellulose acetate phthalate, cellulose acetate succinate, methylcellulose phthate, hydroxymethylethylcellulosephthate, hydroxypropylmethylcellulose phthalate, hydroxypropylmethylcellulose acetate succinate, polyvinyl alcohol phthalate, polyvinyl butylate phthalate, polyvinyl actal phthalate, a copolymer of vinyl acetate/maleic anhydride, a copolymer of styrene/maleic acid monoester, a copolymer of methyl acrylate/methacrylic acid, a copolymer of styrene/acrylic acid, a copolymer of methyl acrylate/methacrylic acid/octyl acrylate, a copolymer of methacrylic acid/methyl methacrylate, benzylaminomethylcellulose, diethylaminomethylcellulose, piperidylethylhydroxyethylcellulose, cellulose acetate dimethylaminoacetate, a copolymer of vinyl diethylamine/vinyl acetate, a copolymer of vinyl benzylamine/vinyl acetate, polyvinyl acetaldiethylamino acetate, a copolymer of vinylpiperidylacetoacetal/vinyl acetate, polydiethylaminomethylstyrene, a copolymer of methyl methacrylate/butyl methacrylate/dimethylaminoethyl methacrylate and polydimethylaminoethyl methacrylate, a copolymer of 2-methy-5vinylpyridine/methylmethacrylate/methacrylic acid, a copolymer of 2-methyl-5-vinylpyridine/methyl acrylate/methacrylic acid, a copolymer of 2-vinyl-5-ethylpyridine/methacrylic acid/methy acrylate, a copolymer of 2-vinylpyrid-ine/methacrylic acid/acrylonitrile, carboxymethylpiperidyl starch, carboxy-methylbenzylaminocellulose, a copolymer of N-vinylglycine/styrene, chitosan, poly(vinyl alcohol), maleic anhydride copolymer, poly (vinyl pyrolidone), starch and starch-based polymers, poly (2-ehtyl-2-oxazoline), poly(ethyleneimine), polyurethane hydrogels, welan gum, rhamsan gum, polyvinyl acetates, ethylcellulose, eudragit RL, RS, NE 30D, Kollicoat EMM 30D, or combinations thereof.

In some embodiments, in conjunction with other above or below embodiments, the control release agent is a polymer.

In some embodiments, in conjunction with other above or below embodiments, the control release agent is selected from pulluan, dextrin, sodium and calcium acid, polyacrylic acid, polymethacrylic acid, polymethylvinylether co-maleic anhydride, polyvinylpyrrolidone, polyethylene oxide, polyethylene glycol, hydroxypropylcellulose, hydroxypropylmethylcellulose, hydroxyethylcellulose, hydroxymethyl methacrylate, sodium carboxymethylcellulose, calcium carboxymethylcellulose, methylcellulose, maltodextrin, xanthan gum, tragacanth gum, agar, gellan gum, kayara gum, alginic acids, pectins, pre-gelatinized starch, polyvinyl alcohol, carboxymethylethylcellulose, cellulose acetate phthalate, cellulose acetate succinate, methylcellulose phthate, hydroxymethylethylcellulosephthate, hydroxypropylmethylcellulose phthalate, hydroxypropylmethylcellulose acetate succinate, polyvinyl alcohol phthalate, polyvinyl butylate phthalate, polyvinyl actal phthalate, a copolymer of vinyl acetate/maleic anhydride, a copolymer of styrene/maleic acid monoester, a copolymer of methyl acrylate/methacrylic acid, a copolymer of styrene/acrylic acid, a copolymer of methyl acrylate/methacrylic acid/octyl acrylate, a copolymer of methacrylic acid/methyl methacrylate, benzylaminomethylcellulose, diethylaminomethylcellulose, piperidylethylhydroxyethylcellulose, cellulose acetate dimethylaminoacetate, a copolymer of vinyl diethylamine/vinyl acetate, a copolymer of vinyl benzylamine/vinyl acetate, polyvinyl acetaldiethylamino acetate, a copolymer of vinylpiperidylacetoacetal/vinyl acetate, polydiethylaminomethylstyrene, a copolymer of methyl methacrylate/butyl methacrylate/dimethylaminoethyl methacrylate and polydimethylaminoethyl methacrylate, a copolymer of 2-methy-5vinylpyridine/methylmethacrylate/methacrylic acid, a copolymer of 2-methyl-5-vinylpyridine/methyl acrylate/methacrylic acid, a copolymer of 2-vinyl-5-ethylpyridine/methacrylic acid/methy acrylate, a copolymer of 2-vinylpyrid-ine/methacrylic acid/acrylonitrile, carboxymethylpiperidyl starch, carboxy-methylbenzylaminocellulose, a copolymer of N-vinylglycine/styrene, chitosan, poly(vinyl alcohol), maleic anhydride copolymer, poly (vinyl pyrolidone), starch and starch-based polymers, poly (2-ehtyl-2-oxazoline), poly(ethyleneimine), polyurethane hydrogels, welan gum, rhamsan gum, polyvinyl acetates, ethylcellulose, eudragit RL, RS, NE 30D, and Kollicoat EMM 30D, or any combination thereof. In various cases, the control release agent comprises methylcellulose, hydroxypropyl methylcellulose, or a combination thereof. Examples of methylcellulose and hydroxypropyl methylcellulose contemplated include METHOCEL K100 MPrem CR, METHOCELL K100 LV Prem CR, and mixtures thereof. METHOCELL K100 MPrem CR is hypromellose having a viscosity of 100,000 mPa/s at 2% concentration in water at 20° C., and METHOCELL K100 LV Prem CR is hypromellose having a viscosity of 100 mPa/s at 2% concentration in water at 20° C.

pH Modifying Agent:

As used herein, the term "pH modifying agent" refers to an agent capable of modulating the pH to a desired range. In some embodiments, in conjunction with other above or below embodiments, the pH modifying agent is an acidifying agent. In some embodiments, in conjunction with other above or below embodiments, the pH modifying agent is present in an amount sufficient to lower the pH. pH Modulation agents include maleic acid, citric acid, tartaric acid, pamoic acid, fumaric acid, salicylic acid, 2,6-diaminohexanoic acid, camphorsulfonic acid, glycerophosphoric acid, 2-hydroxyethanesulfonic acid, isethionic acid, succinic acid, carbonic acid, p-toluenesulfonic acid, aspartic acid, 8-chloro¬theophylline, benezenesulfonic acid, malic acid, orotic acid, oxalic acid, benzoic acid, 2-naphthalenesulfonic acid, stearic acid, adipic acid, p-amino¬salicylic acid, 5-aminoslicylic acid, ascorbic acid, sulfuric acid, cyclamic acid, sodium lauryl sulfate, glucoheptonic acid, glucuronic acid, glycine, sulfuric acid, mandelic acid, 1,5-naphthalenedisulfonic acid, nicotinic acid, oleic acid, 2-oxoglutaric acid, pyridoxal 5-phosphate, undecanoic acid, p-acetamidobenzoic acid, o-acetamido-benzoic acid, m-acetamidobenzoic acid, N-acetyl-L-aspartic acid, camphoric acid, dehydrocholic acid, malonic acid, edetic acid, ethylenediainetetraacetic acid, ethylsulfuric acid, hydroxyphenylbenzoylbenzoic acid, glutamic acid, glycyrrhizic acid, 4-hexylresorcinol, hippuric acid, p-phenolsulfonic acid, 4-hydroxybenzoic acid, 3-hydroxybenzoic acid, 3-hydroxy-2-naphthoic acid, 1-hydroxy-2naphthoic acid, lactobionic acid, 3'-adenylic acid, 5'-adenylic acid, mucic acid, galactaric acid, pantothenic acid, pectic acid, polygalacturonic acid, 5-sulfosalicylic acid, 1,2,3,6-tetrahydro-1,3-dimethyl-2,6-dioxopurine-7-propanesulfonic acid, terephthalic acid, 1-hydroxy-2naphthoic acid, and combinations thereof. In some embodiments, in conjunction with other above or below embodiments, pH modifying agents include, for example, maleic acid, citric acid, malic acid, fumaric acid, sulfuric acid, tartaric acid, lactic acid, salicylic acid, aspartic acid, aminosalicylic acid, malonic acid, glutamic acid, and combinations thereof.

In some embodiments, in conjunction with other above or below embodiments, the pH modifying agent is selected from maleic acid, citric acid, malic acid, fumaric acid, sulfuric acid, tartaric acid, lactoic acid, salicylic acid, aspartic acid, aminosalicylic acid, malonic acid, glutamic acid, and any combination thereof.

In some embodiments, in conjunction with other above or below embodiments, fumaric acid was used as the pH modifying agent as it is less hygroscopic and more compatible with omecamtiv mecarbil dihydrochloride hydrate than citric acid, resulting in less or no active form transformation and no changes in tablet appearance when stored at 40° C./75% RH for 6 months, leading to improved final product quality. Additionally, fumaric acid is more acidic (2-fold) than citric acid. Therefore, it is more efficient, i.e., 1:1 weight ratio to active instead of 2:1, to use fumaric acid to modulate the microenvironmental pH to enhance omecamtiv mecarbil release at neutral environment. Fumaric acid also has a very slow dissolution rate. As a result, fumaric acid will stay in the tablet longer and maintain the low microenvironmental pH better, resulting in more complete release of omecamtiv mecarbil within 24 hours. In some embodiments, then, the pH modifying agent is selected from maleic acid, fumaric acid, tartaric acid, glutamic acid, and any combination thereof. In some embodiments, the pH modifying agent comprises fumaric acid.

Filler:

As used herein, the term "fillers" refers to one or more substances that can be added to components of a pharmaceutical composition to increase bulk weight of the material to be formulated, e.g. tabletted, in order to achieve the desired weight. Fillers include but are not limited to starches, lactose, mannitol (such as Pearlitol™ SD 200), cellulose derivatives, calcium phosphate, sugar and the like.

Different grades of lactose include, but are not limited, to lactose monohydrate, lactose DT (direct tableting), lactose anhydrous, Flowlac™ (available from Meggle products), Pharmatose™ (available from DMV) and others. Different grades of starches include, but are not limited to, maize starch, potato starch, rice starch, wheat starch, pregelatinized starch (commercially available as PCS PC10 from Signet Chemical Corporation) and Starch 1500, Starch 1500 LM grade (low moisture content grade) from Colorcon, fully pregelatinized starch (commercially available as National 78-1551 from Essex Grain Products) and others. Different cellulose compounds that can be used include crystalline cellulose and powdered cellulose. Examples of crystalline cellulose products include but are not limited to CEOLUS™ KG801, Avicel™ PH 101, PH102, PH301, PH302 and PH-F20, microcrystalline cellulose 114, and microcrystalline cellulose 112. Other useful fillers include, but are not limited to, carmellose, sugar alcohols such as mannitol, sorbitol and xylitol, calcium carbonate, magnesium carbonate, dibasic calcium phosphate, and tribasic calcium phosphate.

In some embodiments, in conjunction with other above or below embodiments, the filler is selected from starch, lactose, mannitol (such as Pearlitol™ SD 200), cellulose derivatives, calcium phosphate, and a sugar.

In some embodiments, in conjunction with other above or below embodiments, the filler is lactose anhydrous or lactose monohydrate. In some embodiments, in conjunction with other above or below embodiments, the filler is lactose DT, Flowlac™, or Pharmatose™.

In some embodiments, in conjunction with other above or below embodiments, the filler is maize starch, potato starch, rice starch, wheat starch, pregelatinized starch (such as Starch 1500 or Starch 1500 LM grade (low moisture content grade)), or fully pregelatinized starch.

In some embodiments, in conjunction with other above or below embodiments, the filler is microcrystalline cellulose, such as CEOLUS™ KG801, Avicel™ PH 101, PH102, PH301, PH302 and PH-F20, microcrystalline cellulose 114, or microcrystalline cellulose 112.

In some embodiments, in conjunction with other above or below embodiments, the filler is carmellose, mannitol, sorbitol, xylitol, calcium carbonate, magnesium carbonate, dibasic calcium phosphate, or tribasic calcium phosphate.

Lubricant:

As used herein, the term "lubricants" refers to one or more substances that can be added to components of the present compositions to reduce sticking by a solid formulation to the equipment used for production of a unit doss form. Lubricants include stearic acid, hydrogenated vegetable oils, hydrogenated soybean oil and hydrogenated soybean oil & castor wax, stearyl alcohol, leucine, polyethylene glycol, magnesium stearate, glycerylmonostearate, stearic acid, glycerybehenate, polyethylene glycol, ethylene oxide polymers, sodium lauryl sulfate, magnesium lauryl sulfate, sodium oleate, sodium stearylFumarate, DL-leucine, colloidal silica, and mixtures thereof.

In some embodiments, in conjunction with other above or below embodiments, the lubricant is stearic acid, hydrogenated vegetable oil, hydrogenated soybean oil, hydrogenated soybean oil, castor wax, stearyl alcohol, leucine, polyethylene glycol, magnesium stearate, glycerylmonostearate, stearic acid, glycerybehenate, polyethylene glycol, ethylene oxide polymers, sodium lauryl sulfate, magnesium lauryl sulfate, sodium oleate, sodium stearylfumarate, DL-leucine, colloidal silica, or any mixture thereof.

As will be recognized, the steps of the methods provided herein need not be performed any particular number of times or in any particular sequence. Additional objects, advantages and novel features of the invention(s) will become apparent to those skilled in the art upon examination of the following examples thereof, which are intended to be illustrative and not intended to be limiting.

EXAMPLES

Example 1

Evaluation of Omecamtiv Mecarbil in Anesthetized Dogs with High and Low Heart Rates:

Beagle dogs (male; 10-12 kg) are induced into anesthesia by treatment with morphine (1-2 mg/kg, IM) and alpha-chloralose (80-120 mg/kg IV; solution strength: 10 mg/ml). Immediately following induction, anesthesia is maintained by constant infusion of alpha-chloralose (35-75 mg/kg/hr, IV) for the duration of the study (delivery is controlled with an IV pump). Dogs are intubated with an endotracheal tube and are immediately ventilated with room air by positive respiration (Harvard Large Animal pump; rate: 15 strokes/minute; volume: 100-150 ml/stroke) and assessed by arterial blood gas measurement. Normal core body temperature (37° C.) is maintained with a thermostatically-controlled heating blanket. Intravenous fluids (saline: 2-5 ml/kg/hr) are infused throughout the procedure and a Foley catheter placed in the urinary bladder to assure urine flow.

Cardiovascular Instrumentation:

Bilateral incisions in the neck and inguinal regions are made to insert fluid-filled catheters into the external jugular vein (unilateral or bilateral), carotid artery (unilateral right or left), and a femoral artery and vein (unilateral or bilateral)

using convention vascular cut-down methods. Arterial pressure is recorded from the femoral artery and left ventricular pressure recorded from a solid-state catheter (Millar) inserted via the carotid or femoral artery. A jugular vein cannula is used for blood sampling (drug level determination) and a femoral vein used for infusion of test article. Patency of vascular cannulas is maintained with heparinized saline (50 Units/ml). ECG (lead II and precordial) is recorded from subcutaneous needle electrodes. All cardiovascular signals are captured on a computerized data acquisition system (EMKA iox) and analyzed post-study (EMKA ECGAuto). Ultrasound echocardiography (GE Vivid S6 with a phased array probe; 3.5-8 MHz) images were collected from right parasternal and apical views.

Drug Infusion:

Dogs are stabilized (20 to 30 min) following surgical instrumentation to establish baseline values for all cardiovascular parameters. Test articles was administered through an in-dwelling venous catheter at a constant infusion rate and volume over 30 min with a syringe pump. Each dog was treated with vehicle and six escalating doses of omecamtiv mecarbil (see table).

| Treatment | Dose: number | Dose: mg/kg | Cumulative Dose (mg/kg) |
|---|---|---|---|
| omecamtiv mecarbil | Vehicle | 0 | 0 |
|  | 1 | 0.49 | 0.38 |
|  | 2 | 0.40 | 0.89 |
|  | 3 | 0.49 | 1.38 |
|  | 4 | 0.72 | 2.1 |
|  | 5 | 0.875 | 2.97 |

Heart Rate Pacing:

Omecamtiv mecarbil is administered to two groups of dogs: group 1 with low heart rate values (50-60 bpm) and group 2 with elevated heart rate (~120 bpm) maintained by a cardiac pacemaker inserted into the right ventricle (via the jugular vein). In each group, changes in ejection faction (or fractional shortening) and systolic and diastolic time intervals induced by omecamtiv mecarbil are compared in dogs with high and low heart rates. Dogs with low heart rate emulate treatment with ivabradine.

Plasma Drug Level:

Blood samples (1-2 mL) are taken at baseline (pre-infusion) and during each omecamtiv mecarbil infusion period (e.g., 10, 20 and 29 min time points) for determination of drug level. The blood samples are collected in tubes treated with an anticoagulant (EDTA) and then maintained on wet ice prior to centrifugation to obtain plasma. Plasma samples are then frozen and transferred for bioanalysis.

Example 2

Healthy male beagle dogs (n=7) instrumented with radio-telemetry units providing continuous single-lead electrocardiogram (ECG), as well as systemic (arterial, AoP) and left-ventricular (LVP) pressure signals were used for this study. Following sling acclimation, the animals were assigned to receive repeated oral (via gavage) treatments with either Ivabradine (IVA, 5 mg/kg bid) or a volume-matched placebo-control (sterile water, CTRL) for 5 days, administered at a dose volume of 10 mL/kg, in a cross over design.

The animals were sling-restrained and were subjected to acute intravenous administration of either sterile water (VEH, on Days 4 and 11 of dosing) or Omecamtiv Mecarbil (OM, on Days 5 and 12 of dosing). OM treatments were performed over a 3-hour infusion duration, following a dose-escalation design targeting plasma concentrations of 600 and 1000 ng/mL (each over 90 minutes, with a 30 minute loading infusion followed by a 60 minute maintenance infusion) for a cumulative dose of 5.293 mg/kg (as shown in Table A below). The IV vehicle treatments were time- and volume-matched.

TABLE A

| OM Infusion | | OM Dose (mg/kg) | Cumulative OM Dose (mg/kg) | Start Time (hours) | End Time (hours) | Target Plasma Conc. (ng/mL) | Dose Vol (mL/kg/0.5 hour) |
|---|---|---|---|---|---|---|---|
| OM | D1 | 1.112 | 1.112 | 0 | 0.5 | 600 | 0.326 |
|  | D2 | 1.362 | 2.474 | 0.5 | 1.5 | 600 | 0.199 |
|  | D3 | 1.112 | 3.586 | 1.5 | 2 | 1000 | 0.326 |
|  | D4 | 1.707 | 5.293 | 2 | 3 | 1000 | 0.250 |

Telemetered data were collected continuously for at least 90 minutes prior to and during dosing, as well as for at least 20 hours post-dose. The LVP and ECG signals were digitized at a sampling rate of at least 1000 Hz. The data were analyzed for heart rate (HR) and left-ventricular hemodynamic/mechanical indices that were obtained from the pressure waveform, including mean systolic (MSP) and end-diastolic (filling, EDP) pressures, the peak rates of pressure change during systole/diastole ($dP/dt_{max/min}$), as well as the time-constant of relaxation (tau) and a contractility index (CI: $dP/dt_{max}$ normalized by the pressure at $dP/dt_{max}$). The data were also analyzed for systolic and diastolic intervals, including the estimated durations of the systolic ejection (SET), contraction (CT), active relaxation (RT) and filling intervals (FT), as well as the systolic-to-diastolic interval ratio (S/D: SET/RT+FT), which were derived from the left-ventricular pressure waveform.

The left-ventricular indices were evaluated only in the sling-restrained animals before and during IV treatment with OM or vehicle. Cardiovascular responses at each dose level were monitored for up to 90 minutes, i.e., over 3 hours total (during IV dosing of VEH and OM on Days 4, 5, 11, and 12 in the dose administration paradigm). Overall, in-sling cardiovascular data are reported at the following pre-determined/targeted time points: prior to dosing (i.e., at baseline, PRE) and approximately at the end of each infusion period (i.e., up to 4 time points during dosing, D1 to D4). Signals were analyzed continuously in 5-minute epochs, with pre-administration (i.e., PRE) values representing the overall mean over at least 5-epochs (i.e., 25 minutes) taken immediately prior to the onset of dosing, while during-dosing values reflect 5-minute averages (i.e., 1 epoch) taken prior to the (estimated) termination of each infusion. Data are presented as both means with standard deviations in summarizing tables/figure; beat-to-beat plots against heart rate are part of the study file.

Table 1 shows effects of repeated treatment with Ivabradine (IVA, 5 mg/kg bid for at least 5 days) on left-ventricular hemodynamics, as well as load-dependent mechanical and timing indices derived from the left-ventricular pressure signal, as measured at baseline in the conscious sling-restrained telemetered canine preparation; data for volume-/time-matched placebo-controls (sterile water, CTRL) are shown for comparison.

Control (Oral) Treatment:

Quantitatively, the hemodynamic and mechanical state of the individual dogs at the start of the experiments (i.e., at baseline) were considered to be within the normal physiological range for the species, as well as in good agreement with previously reported values (e.g., Table 1). In dogs given oral vehicle for 4 days (control values), the average values for heart rate (HR), mean systolic pressure (MSP), and peak-rate of left-ventricular pressure-change during systole (i.e., dP/dt) values prior to dosing were 108±7 bpm, 132±1 mmHg, and 2,464±86 mmHg/s (respectively). Similarly, average left-ventricular end-diastolic (filling) pressures (EDP: 12±2 mmHg) were consistent with normal cardiac function.

Values are the mean±standard error of the mean for ensemble averages taken either before (PRE, at least a 25-min average), and/or during dosing (D1-D4, 5-min average) with either vehicle (VEH, n=7) or Omecamtiv Mecarbil (OM, n=7); relative (%) changes from pre-dosing values in italics. OM treatments were performed over 3 hours following a two-dose escalating design targeting plasma concentrations of 600 and 1000 ng/mL, each over 90 minutes, with a 30-min loading infusion (D1 and D3) followed by a 60-min maintenance infusion (D2 and D4) for a cumulative dose of 5.293 mg/kg; vehicle treatments were time- and volume-matched.

TABLE 1

|  | Parameter (units) | CTRL (n = 7) | IVA (n = 7) | P-value* |
|---|---|---|---|---|
| Mechanical | HR (bpm) | 108 ± 7 | 82 ± 5 (−24 ± 3) | 0.001 |
|  | LV-EDP (mmHg) | 12 ± 2 | 16 ± 2 (40 ± 12) | 0.012 |
|  | LV-MSP (mmHg) | 132 ± 1 | 137 ± 3 (4 ± 2) | 0.075 |
|  | LV-dP/dt$_{max}$ (mmHg/s) | 2,464 ± 86 | 2,644 ± 79 (8 ± 3) | 0.026 |
|  | LV-dP/dt$_{min}$ (mmHg/s) | −2,205 ± 68 | −2,367 ± 68 (8 ± 3) | 0.056 |
|  | LV-V$_{max}$ (1/s) | 35.5 ± 1.5 | 37.0 ± 1.0 (5 ± 3) | 0.145 |
|  | LV-Tau (ms) | 29.8 ± 2.4 | 28.5 ± 1.4 (−3 ± 3) | 0.338 |
| Cardiac Timing+ | SET (ms) | 151 ± 5 | 157 ± 2 (4 ± 2) | 0.131 |
|  | CT (ms) | 68 ± 1 | 61 ± 1 (−9 ± 1) | 0.001 |
|  | FT (ms) | 332 ± 41 | 577 ± 49 (81 ± 13) | <0.001 |
|  | RT (ms) | 90 ± 2 | 88 ± 1 (−2 ± 2) | 0.220 |
|  | S/D (n/u) | 0.38 ± 0.03 | 0.24 ± 0.01 (−35 ± 3) | <0.001 |

Values are the mean ± standard error of the mean, estimated the left-ventricular pressure signal (LVP). Data are mean pre-dosing averages taken across study days 4/5 (CTRL/IVA) and/or across study days 11/12 (IVA/CTRL).
+SET: systolic ejection time; CT: contraction time; FT: filling time; RT: relaxation time; S/D: systolic to diastolic ratio (SET/RT + FT); n/u: no unit.
*via a two-tailed paired Student's t-test (SigmaPlot 12.3; SysStat Software, Inc.)

Table 2A shows left-ventricular end-diastolic (EDP) and mean systolic pressures (MSP) as well as the respective peak rates of change during diastole/systole (dP/dt$_{min}$, dP/dt$_{max}$) as measured before and during acute intravenous administration of either vehicle (VEH, sterile water) or Omecamtiv Mecarbil (OM) in conscious telemetered beagle dogs in the setting of repeated placebo therapy (CTRL, sterile water for at least 5 days).

Table 2B shows left-ventricular end-diastolic (EDP) and mean systolic pressures (MSP) as well as the respective peak rates of change during diastole/systole (dP/dt$_{min}$, dP/dt$_{max}$) as measured before and during acute intravenous administration of either vehicle (VEH, sterile water) or Omecamtiv Mecarbil (OM) in conscious telemetered beagle dogs in the setting of repeated Ivabradine therapy (IVA, 5 mg/kg bid, for at least 5 days).

TABLE 2A

|  |  | Time Point (dose level) | | | | |
|---|---|---|---|---|---|---|
|  | Group | PRE | D1 | D2 | D3 | D4 |
| HR (bpm) | VEH | 113 ± 7 | 108 ± 7 | 103 ± 5 | 93 ± 6 | 103 ± 8 |
|  | % vs. PRE | — | −4 ± 6 | −8 ± 3 | −16 ± 6 | −8 ± 6 |
|  | OM | 102 ± 8 | 86 ± 6 | 99 ± 9 | 112 ± 12 | 162 ± 14 |
|  | % vs. PRE | — | −14 ± 7 | 0 ± 11 | 11 ± 10 | 65 ± 20 |
| EDP (mmHg) | VEH | 11.8 ± 2.0 | 10.1 ± 1.6 | 11.1 ± 1.3 | 10.9 ± 1.6 | 12.1 ± 1.4 |
|  | % vs. PRE | — | −14 ± 9 | 0 ± 7 | −4 ± 8 | 13 ± 14 |
|  | OM | 12.3 ± 1.9 | 9.8 ± 2.1 | 8.5 ± 1.8 | 10.8 ± 1.9 | 17.8 ± 4.2 |
|  | % vs. PRE | — | −24 ± 7 | −33 ± 5 | −13 ± 10 | 46 ± 33 |
| MSP (mmHg) | VEH | 133 ± 3 | 132 ± 3 | 135 ± 2 | 132 ± 3 | 137 ± 2 |
|  | % vs. PRE | — | 0 ± 3 | 2 ± 3 | 0 ± 4 | 4 ± 2 |
|  | OM | 131 ± 2 | 127 ± 1 | 130 ± 2 | 130 ± 2 | 111 ± 8 |
|  | % vs. PRE | — | −2 ± 2 | 0 ± 2 | 0 ± 2 | −15 ± 6 |
| dP/dt$_{max}$ (mmHg/s) | VEH | 2,526 ± 90 | 2,482 ± 103 | 2,496 ± 104 | 2,376 ± 119 | 2,486 ± 80 |
|  | % vs. PRE | — | −2 ± 4 | −1 ± 3 | −6 ± 4 | −1 ± 2 |
|  | OM | 2,401 ± 111 | 2,243 ± 81 | 2,356 ± 114 | 2,319 ± 127 | 1,844 ± 215 |
|  | % vs. PRE | — | −6 ± 3 | −1 ± 4 | −3 ± 3 | −23 ± 8 |
| dP/dt$_{min}$ (mmHg/s) | VEH | −2,244 ± 80 | −2,245 ± 76 | −2,245 ± 80 | −2,186 ± 101 | −2,261 ± 65 |
|  | % vs. PRE | — | 0 ± 3 | 0 ± 3 | −2 ± 5 | 1 ± 2 |
|  | OM | −2,167 ± 81 | −1,910 ± 78 | −1,759 ± 120 | −1,608 ± 127 | −1,288 ± 197 |
|  | % vs. PRE | — | −12 ± 3 | −19 ± 4 | −26 ± 4 | −41 ± 8 |

TABLE 2B

| | Group | PRE | D1 | D2 | D3 | D4 |
|---|---|---|---|---|---|---|
| HR (bp) | IVA + VEH | 85 ± 5 | 76 ± 4 | 76 ± 4 | 69 ± 3 | 74 ± 5 |
| | % vs. PRE | — | −9 ± 3 | −9 ± 4 | −17 ± 6 | −12 ± 4 |
| | IVA + OM | 79 ± 5 | 74 ± 5 | 69 ± 6 | 67 ± 4 | 84 ± 4 |
| | % vs. PRE | — | −7 ± 2 | −13 ± 4 | −14 ± 6 | 10 ± 10 |
| EDP (mmHg) | IVA + VEH | 15.7 ± 1.6 | 14.4 ± 1.9 | 15.3 ± 1.1 | 14.5 ± 1.3 | 14.2 ± 1.6 |
| | % vs. PRE | — | −10 ± 4 | 0 ± 7 | −4 ± 11 | −9 ± 9 |
| | IVA + OM | 15.7 ± 1.7 | 14.2 ± 1.6 | 12.3 ± 1.6 | 10.8 ± 1.5 | 12.7 ± 1.0 |
| | % vs. PRE | — | −10 ± 4 | −22 ± 5 | −31 ± 7 | −16 ± 6 |
| MSP (mmHg) | IVA + VEH | 138 ± 3 | 138 ± 3 | 145 ± 2 | 143 ± 4 | 143 ± 2 |
| | % vs. PRE | — | 0 ± 1 | 5 ± 1 | 3 ± 2 | 4 ± 2 |
| | IVA + OM | 136 ± 4 | 145 ± 6 | 143 ± 6 | 136 ± 3 | 140 ± 6 |
| | % vs. PRE | — | 6 ± 2 | 5 ± 2 | 0 ± 2 | 3 ± 3 |
| $dP/dt_{max}$ (mmHg/s) | IVA + VEH | 2,661 ± 95 | 2,606 ± 97 | 2,704 ± 63 | 2,662 ± 93 | 2,702 ± 81 |
| | % vs. PRE | — | −2 ± 2 | 2 ± 2 | 0 ± 3 | 2 ± 3 |
| | IVA + OM | 2,626 ± 77 | 2,588 ± 72 | 2,475 ± 89 | 2,327 ± 55 | 2,426 ± 48 |
| | % vs. PRE | — | −1 ± 2 | −6 ± 2 | −11 ± 2 | −7 ± 2 |
| $dP/dt_{min}$ (mmHg/s) | IVA + VEH | −2,407 ± 93 | −2,365 ± 82 | −2,492 ± 67 | −2,425 ± 89 | −2,457 ± 81 |
| | % vs. PRE | — | −2 ± 1 | 4 ± 2 | 1 ± 2 | 2 ± 3 |
| | IVA + OM | −2,327 ± 100 | −2,293 ± 117 | −2,063 ± 131 | −1,686 ± 105 | −1,556 ± 57 |
| | % vs. PRE | — | −2 ± 3 | −12 ± 2 | −28 ± 2 | −33 ± 1 |

Values are the mean±standard error of the mean, for ensemble averages taken either before (PRE, at least a 25-min average), and/or during dosing (D1-D4, 5-min average) with either vehicle (VEH, n=7) or Omecamtiv Mecarbil (OM, n=7); relative (%) changes from pre-dosing values in italics. OM treatments were performed over 3 hours following a two-dose escalating design targeting plasma concentrations of 600 and 1000 ng/mL, each over 90 minutes, with a 30-min loading infusion (D1 and D3) followed by a 60-min maintenance infusion (D2 and D4) for a cumulative dose of 5.293 mg/kg; vehicle treatments were time- and volume-matched.

Table 3A shows estimated maximal velocity of myocardial contractile-element shortening ($V_{max}$) and left-ventricular relaxation time-constant (Tau) derived/estimated from left-ventricular pressures as measured before and during acute intravenous administration of either vehicle (VEH, sterile water) or Omecamtiv Mecarbil (OM) in conscious telemetered beagle dogs in the setting of repeated placebo therapy (CTRL, sterile water for at least 5 days).

TABLE 3A

| | Group | PRE | D1 | D2 | D3 | D4 |
|---|---|---|---|---|---|---|
| $V_{max}$ (1/s) | VEH | 36.1 ± 1.4 | 36.3 ± 1.1 | 35.6 ± 1.3 | 35.0 ± 1.3 | 35.2 ± 1.1 |
| | % vs. PRE | — | 1 ± 2 | −1 ± 2 | −3 ± 3 | −2 ± 3 |
| | OM | 34.9 ± 1.6 | 36.0 ± 1.7 | 37.2 ± 1.6 | 35.6 ± 2.0 | 28.4 ± 3.4 |
| | % vs. PRE | — | 3 ± 1 | 7 ± 2 | 2 ± 2 | −19 ± 8 |
| Tau (ms) | VEH | 28.8 ± 2.1 | 28.0 ± 1.8 | 30.1 ± 2.3 | 31.0 ± 2.2 | 30.8 ± 2.1 |
| | % vs. PRE | — | −2 ± 2 | 5 ± 3 | 8 ± 4 | 8 ± 5 |
| | OM | 30.8 ± 2.8 | 36.7 ± 3.6 | 41.1 ± 4.7 | 47.6 ± 6.5 | 54.7 ± 9.7 |
| | % vs. PRE | — | 19 ± 3 | 33 ± 5 | 53 ± 7 | 72 ± 16 |

Values are the mean±standard error of the mean, for ensemble averages taken either before (PRE, at least a 25-min average), and/or during dosing (D1-D4, 5-min average) with either vehicle (VEH, n=7) or Omecamtiv Mecarbil (OM, n=7); relative (%) changes from pre-dosing values in italics. OM treatments were performed over 3 hours following a two-dose escalating design targeting plasma concentrations of 600 and 1000 ng/mL, each over 90 minutes, with a 30-min loading infusion (D1 and D3) followed by a 60-min maintenance infusion (D2 and D4) for a cumulative dose of 5.293 mg/kg; vehicle treatments were time- and volume-matched.

Table 3B shows estimated maximal velocity of myocardial contractile-element shortening ($V_{max}$) and left-ventricular relaxation time-constant (Tau) derived/estimated from left-ventricular pressures as measured before and during acute intravenous administration of either vehicle (VEH, sterile water) or Omecamtiv Mecarbil (OM) in the setting of repeated Ivabradine therapy (IVA, 5 mg/kg bid, for at least 5 days).

TABLE 3B

| | Group | PRE | D1 | D2 | D3 | D4 |
|---|---|---|---|---|---|---|
| $V_{max}$ (1/s) | IVA + VEH | 37.1 ± 1.1 | 36.9 ± 1.3 | 36.7 ± 0.8 | 37.2 ± 0.7 | 37.3 ± 1.0 |
| | % vs. PRE | — | 0 ± 1 | −1 ± 1 | 1 ± 2 | 1 ± 1 |
| | IVA + OM | 37.0 ± 1.0 | 36.9 ± 1.1 | 37.0 ± 1.1 | 37.3 ± 1.1 | 35.5 ± 1.4 |
| | % vs. PRE | — | 0 ± 1 | 0 ± 1 | 1 ± 3 | −4 ± 4 |
| Tau (ms) | IVA + VEH | 27.9 ± 1.4 | 28.7 ± 1.7 | 29.3 ± 1.0 | 29.2 ± 1.0 | 28.8 ± 1.5 |
| | % vs. PRE | — | 3 ± 2 | 6 ± 2 | 5 ± 3 | 3 ± 2 |
| | IVA + OM | 29.2 ± 1.4 | 33.9 ± 1.6 | 38.3 ± 2.0 | 46.7 ± 3.3 | 50.0 ± 2.7 |
| | % vs. PRE | — | 16 ± 2 | 31 ± 4 | 60 ± 8 | 72 ± 8 |

Values are the mean±standard error of the mean, for ensemble averages taken either before (PRE, at least a 25-min average), and/or during dosing (D1-D4, 5-min average) with either vehicle (VEH, n=7) or Omecamtiv Mecarbil (OM, n=7); relative (%) changes from pre-dosing values in italics. OM treatments were performed over 3 hours following a two-dose escalating design targeting plasma concentrations of 600 and 1000 ng/mL, each over 90 minutes, with a 30-min loading infusion (D1 and D3) followed by a 60-min maintenance infusion (D2 and D4) for a cumulative dose of 5.293 mg/kg; vehicle treatments were time- and volume-matched.

Table 4A shows durations for the left-ventricular systolic mechanical ejection (SET), contraction (CT), filling (FT), and relaxation (RT) as well as the systolic-to-diastolic mechanical cardiac cycle duration ratio (S/D) as estimated from the left-ventricular pressure waveform before and during acute intravenous administration of either vehicle (VEH, sterile water) or Omecamtiv Mecarbil (OM) in conscious telemetered beagle dogs in the setting of repeated placebo therapy (CTRL, sterile water for at least 5 days).

italics. OM treatments were performed over 3 hours following a two-dose escalating design targeting plasma concentrations of 600 and 1000 ng/mL, each over 90 minutes, with a 30-min loading infusion (D1 and D3) followed by a 60-min maintenance infusion (D2 and D4) for a cumulative dose of 5.293 mg/kg; vehicle treatments were time- and volume-matched.

Table 4B shows durations for the left-ventricular systolic mechanical ejection (SET), contraction (CT), filling (FT), and relaxation (RT) as well as the systolic-to-diastolic mechanical cardiac cycle duration ratio (S/D) as estimated from the left-ventricular pressure waveform before and

TABLE 4A

| | | \multicolumn{5}{c}{Time Point (dose level)} | | | | |
|---|---|---|---|---|---|---|
| | Group | PRE | D1 | D2 | D3 | D4 |
| SET (ms) | VEH | 146 ± 4 | 150 ± 4 | 155 ± 4 | 160 ± 4 | 158 ± 6 |
| | % vs. PRE | — | 2 ± 3 | 6 ± 2 | 10 ± 4 | 8 ± 4 |
| | OM | 156 ± 7 | 207 ± 10 | 214 ± 11 | 208 ± 12 | 162 ± 11 |
| | % vs. PRE | — | 33 ± 3 | 37 ± 6 | 34 ± 6 | 5 ± 8 |
| CT (ms) | VEH | 67.6 ± 0.9 | 67.1 ± 0.7 | 68.5 ± 0.5 | 67.6 ± 0.8 | 68.1 ± 0.8 |
| | % vs. PRE | — | −1 ± 1 | 1 ± 1 | 0 ± 1 | 1 ± 1 |
| | OM | 67.9 ± 0.7 | 65.9 ± 0.6 | 66.7 ± 0.8 | 67.0 ± 1.2 | 71.0 ± 1.4 |
| | % vs. PRE | — | −3 ± 1 | −2 ± 1 | −1 ± 2 | 5 ± 2 |
| FT (ms) | VEH | 294 ± 40 | 314 ± 34 | 358 ± 57 | 429 ± 57 | 347 ± 47 |
| | % vs. PRE | — | 11 ± 12 | 23 ± 8 | 57 ± 29 | 25 ± 20 |
| | OM | 370 ± 50 | 425 ± 54 | 321 ± 60 | 251 ± 39 | 85 ± 35 |
| | % vs. PRE | — | 23 ± 19 | 2 ± 28 | −27 ± 13 | −71 ± 12 |
| RT (ms) | VEH | 88 ± 2 | 88 ± 2 | 91 ± 3 | 93 ± 3 | 93 ± 3 |
| | % vs. PRE | — | 0 ± 1 | 4 ± 2 | 6 ± 2 | 5 ± 3 |
| | OM | 92 ± 3 | 104 ± 4 | 110 ± 4 | 114 ± 7 | 93 ± 7 |
| | % vs. PRE | — | 13 ± 2 | 20 ± 3 | 24 ± 5 | 1 ± 7 |
| S/D (n/u) | VEH | 0.40 ± 0.03 | 0.39 ± 0.03 | 0.37 ± 0.03 | 0.33 ± 0.03 | 0.38 ± 0.03 |
| | % vs. PRE | — | −3 ± 5 | −8 ± 4 | −18 ± 7 | −3 ± 8 |
| | OM | 0.36 ± 0.03 | 0.41 ± 0.03 | 0.5 ± 0.05 | 0.60 ± 0.05 | 1.06 ± 0.12 |
| | % vs. PRE | — | 18 ± 11 | 59 ± 21 | 73 ± 16 | 216 ± 52 |

Values are the mean±standard error of the mean for ensemble averages taken either before (PRE, at least a 25-min average), and/or during dosing (D1-D4, 5-min average) with either vehicle (VEH, n=7) or Omecamtiv Mecarbil (OM, n=7); relative (%) changes from pre-dosing values in italics. OM treatments were performed over 3 hours following a two-dose escalating design targeting plasma concentrations of 600 and 1000 ng/mL, each over 90 minutes, with a 30-min loading infusion (D1 and D3) followed by a 60-min maintenance infusion (D2 and D4) for a cumulative dose of 5.293 mg/kg; vehicle treatments were time- and volume-matched.

during acute intravenous administration of either vehicle (VEH, sterile water) or Omecamtiv Mecarbil (OM) in conscious telemetered beagle dogs in the setting of repeated Ivabradine therapy (IVA, 5 mg/kg bid, for at least 5 days).

TABLE 4B

| | | \multicolumn{5}{c}{Time Point (dose level)} | | | | |
|---|---|---|---|---|---|---|
| | Group | PRE | D1 | D2 | D3 | D4 |
| SET (ms) | IVA + VEH | 155 ± 2 | 161 ± 2 | 163 ± 1 | 167 ± 3 | 165 ± 3 |
| | % vs. PRE | — | 4 ± 2 | 6 ± 2 | 8 ± 3 | 7 ± 2 |
| | IVA + OM | 158 ± 3 | 202 ± 4 | 232 ± 8 | 233 ± 10 | 216 ± 11 |
| | % vs. PRE | — | 28 ± 1 | 46 ± 4 | 48 ± 6 | 37 ± 8 |
| CT (ms) | IVA + VEH | 61.4 ± 0.6 | 63.8 ± 1.6 | 67.2 ± 2.9 | 64.9 ± 2.4 | 67.9 ± 2.6 |
| | % vs. PRE | — | 4 ± 2 | 9 ± 4 | 6 ± 4 | 11 ± 3 |
| | IVA + OM | 61.3 ± 0.6 | 67.6 ± 3.2 | 65.5 ± 0.8 | 64.4 ± 0.5 | 70.5 ± 6.2 |
| | % vs. PRE | — | 10 ± 5 | 7 ± 2 | 5 ± 2 | 15 ± 11 |
| FT (ms) | IVA + VEH | 535 ± 46 | 586 ± 33 | 571 ± 42 | 651 ± 58 | 577 ± 52 |
| | % vs. PRE | — | 11 ± 5 | 8 ± 7 | 24 ± 10 | 9 ± 8 |
| | IVA + OM | 618 ± 54 | 561 ± 54 | 595 ± 57 | 574 ± 43 | 344 ± 37 |
| | % vs. PRE | — | −9 ± 3 | −4 ± 6 | −4 ± 9 | −41 ± 9 |
| RT (ms) | IVA + VEH | 87 ± 1 | 88 ± 1 | 90 ± 1 | 92 ± 1 | 91 ± 1 |
| | % vs. PRE | — | 1 ± 1 | 4 ± 1 | 6 ± 2 | 5 ± 1 |
| | IVA + OM | 88 ± 1 | 101 ± 2 | 108 ± 2 | 120 ± 3 | 121 ± 3 |
| | % vs. PRE | — | 14 ± 1 | 22 ± 2 | 36 ± 3 | 37 ± 4 |
| S/D (n/u) | IVA + VEH | 0.26 ± 0.01 | 0.2 ± 0.01 | 0.25 ± 0.02 | 0.23 ± 0.01 | 0.25 ± 0.02 |
| | % vs. PRE | — | −4 ± 3 | 0 ± 4 | −8 ± 7 | 0 ± 4 |
| | IVA + OM | 0.23 ± 0.02 | 0.32 ± 0.02 | 0.34 ± 0.03 | 0.34 ± 0.01 | 0.48 ± 0.04 |
| | % vs. PRE | — | 37 ± 3 | 48 ± 5 | 50 ± 8 | 111 ± 19 |

Values are the mean±standard error of the mean for ensemble averages taken either before (PRE, at least a 25-min average), and/or during dosing (D1-D4, 5-min average) with either vehicle (VEH, n=7) or Omecamtiv Mecarbil (OM, n=7); relative (%) changes from pre-dosing values in italics. OM treatments were performed over 3 hours following a two-dose escalating design targeting plasma concentrations of 600 and 1000 ng/mL, each over 90 minutes, with a 30-min loading infusion (D1 and D3) followed by a 60-min maintenance infusion (D2 and D4) for a cumulative dose of 5.293 mg/kg; vehicle treatments were time- and volume-matched.

Ivabradine (Oral) Treatment Alone:

In conscious beagles, repeated oral administration of IVA markedly decreased heart rate (HR: −24±3%, $P<0.05$) and prolonged left-ventricular filling times (FT: +81±13%, $P<0.05$), effectively decreasing the mechanical systole-to-diastole duration ratio (S/D: −35±3%, $P<0.05$) and suggesting improved/increased filling. Indeed, both end-diastolic filling pressures (EDP: +40±12%, $P<0.05$) and $dP/dt_{max}$, a preload-dependent inotropic index (+8±3%, $P<0.05$), increased with IVA therapy (Table 1). These chronotropic and mechanical changes are consistent with the known pharmacology of ivabradine.

Omecamtiv Mecarbil (Intravenous) Treatment Alone:

Acute OM administration (IV) in conscious beagles caused dose-dependent prolongation of systolic ejection time and the time-constant of relaxation, while increasing the mechanical systole-to-diastole duration ratio and producing negligible changes in mechanical indices (FIG. 1). For instance, at the dose level expected to produce a steady 600 ng/mL plasma concentration (i.e., at D2), systolic ejection time increased +37±6% (vs. +6±2% in VEH), prolonging the mechanical systole-to-diastole ratio by +59±21% (vs. −8±4% in VEH), while $dP/dt_{max}$ changed only −1±4% (vs. −1±3% in VEH). At the highest dose level assayed (D4, targeted plasma concentration of 1000 ng/mL), OM triggered marked cardio-acceleration (+65±20% vs. −8±6% in VEH) and acute depression in load-dependent inotropic indices (e.g., $V_{max}$: −19±8 vs. −2±3% in VEH) suggesting an acute functional impairment, likely as a consequence of impaired filling/relaxation (e.g., S/D: +216±52 vs. −3±8% in VEH, and tau: +72±16 vs. +8±5% in VEH).

Ivabradine (Oral) and Omecamtiv Mecarbil (Intravenous) Treatment Combination: The overall effects of OM (e.g., prolongation of systolic/relaxation times) appeared vastly preserved in the setting of WA therapy. For instance, at the dose level expected to produce a steady 600 ng/mL plasma concentration (i.e., at D2), systolic ejection increased +46±4% (vs. +6±2% in VEH), prolonging the mechanical systole-to-diastole ratio +48±5% (vs. 0±4% in VEH). However, at the highest OM dose level, the concomitant WA administration not only blunted OM-induced changes in the systolic-to-diastolic duration ratio (+111±19 vs. +216±52% in OM alone), but also seemed to abolish both the triggered cardio-acceleration (+10±10 vs. +65±20% in OM alone) and the acute functional deterioration observed at the highest OM dose level (e.g., for $V_{max}$: −4±4 vs. −19±8% in OM alone).

Given that WA did not prevent the OM-induced changes in relaxation (tau: +72±8 vs. +72±16% in OM alone), these actions are likely attributed to the IVA-mediated negative chronotropy, and associated prolongation in ventricular filling times.

Other uses of the disclosed methods will become apparent to those in the art based upon, inter alia, a review of this patent document.

What is claimed:

1. A method of treating a subject suffering from heart failure comprising administering to the subject omecamtive mecarbil, or a pharmaceutically acceptable salt or hydrate thereof, and ivabradine, or a pharmaceutically acceptable salt or hydrate thereof, wherein the omecamtiv mecarbil or pharmaceutically acceptable salt of hydrate thereof is administered in a total daily amount of 12.5 mg to 75 mg, and the ivabradine or pharmaceutically acceptable salt or hydrate thereof is administered in a total daily amount of 2.5 mg to 20 mg.

2. The method of claim 1, wherein the omecamtiv mecarbil or pharmaceutically acceptable salt or hydrate thereof is administered orally.

3. The method of claim 1, wherein the ivabradine or pharmaceutically acceptable salt or hydrate thereof is administered orally.

4. The method of claim 1, wherein the subject suffers from congestive heart failure.

5. The method of claim 1, wherein the subject suffers from systolic heart failure.

6. The method of claim 1, wherein the subject suffers from heart failure with reduced left ventricular ejection fraction.

* * * * *